US Patent Number: 4,676,771
Date of Patent: Jun. 30, 1987
Henke

[54] ARTERIAL BLOOD FILTER

[75] Inventor: Arthur Henke, Ann Arbor, Mich.
[73] Assignee: Gelman Sciences, Inc., Ann Arbor, Mich.
[21] Appl. No.: 846,072
[22] Filed: Mar. 31, 1986
[51] Int. Cl.[4] ............................................. A61M 37/00
[52] U.S. Cl. ...................................... 604/4; 210/927
[58] Field of Search ........................................ 604/4–6; 55/199, 201; 210/349, 927

[56] References Cited
U.S. PATENT DOCUMENTS

| | | | |
|---|---|---|---|
| 4,056,476 | 11/1977 | Monwen et al. | 210/927 |
| 4,411,783 | 10/1983 | Dickens et al. | 210/927 |
| 4,490,254 | 12/1984 | Gordon et al. | 210/927 |
| 4,517,090 | 5/1985 | Kersten et al. | 604/4 |
| 4,572,724 | 2/1986 | Rosenberg et al. | 604/126 |

Primary Examiner—C. Fred Rosenbaum
Assistant Examiner—Gene B. Kartchner
Attorney, Agent, or Firm—Arnold, White & Durkee

[57] ABSTRACT

An arterial blood filter assembly (10) for removing undissolved gases and foreign bodies, particles, clots, etc., from blood flowing through the assembly (10) includes a housing (34) having an inlet (38) and outlet (44) and a vent (48) for venting undissolved gases from the housing (34). A filter media (60) is supported within the housing (34). The assembly (10) includes a blood flow dividing mechanism disposed between the inlet (38) and filter media (58) to divide blood flow from the inlet (38) into a plurality of spaced inlet streams flowing over and down the outer boundary of the filter media (52) into the tapering space between the media and housing wall, which causes the streams to spread sideways and meet, forming upward-flowing streams which carry the entrained bubbles upward, to the channels in the housing top (80) which direct the air bubbles to the vent (48).

A method for removing undissolved gases from flowing blood in a filter assembly (10) includes the steps of dividing the inlet blood flow into the assembly (10) into a plurality of spaced inlet streams, filtering the undissolved gases from the flowing blood, forming a portion of the blood flow containing the filtered undissolved gases into return streams between the spaced inlet streams, thus allowing the bubbles of undissolved gases to collect in regions of lower velocity near the housing top (80) and flow freely in the formed channels in the housing top (80) to the vent (48).

23 Claims, 8 Drawing Figures

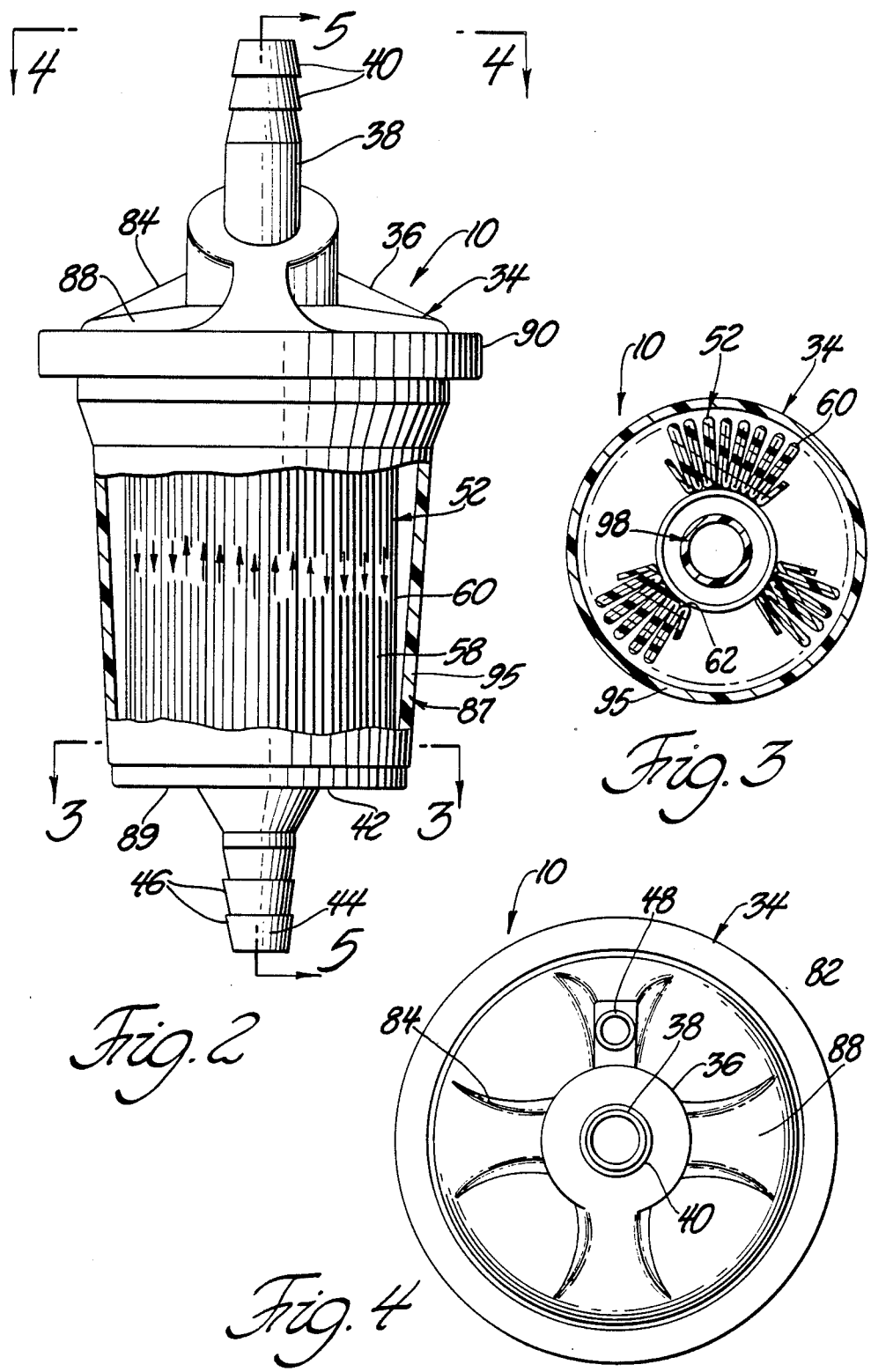

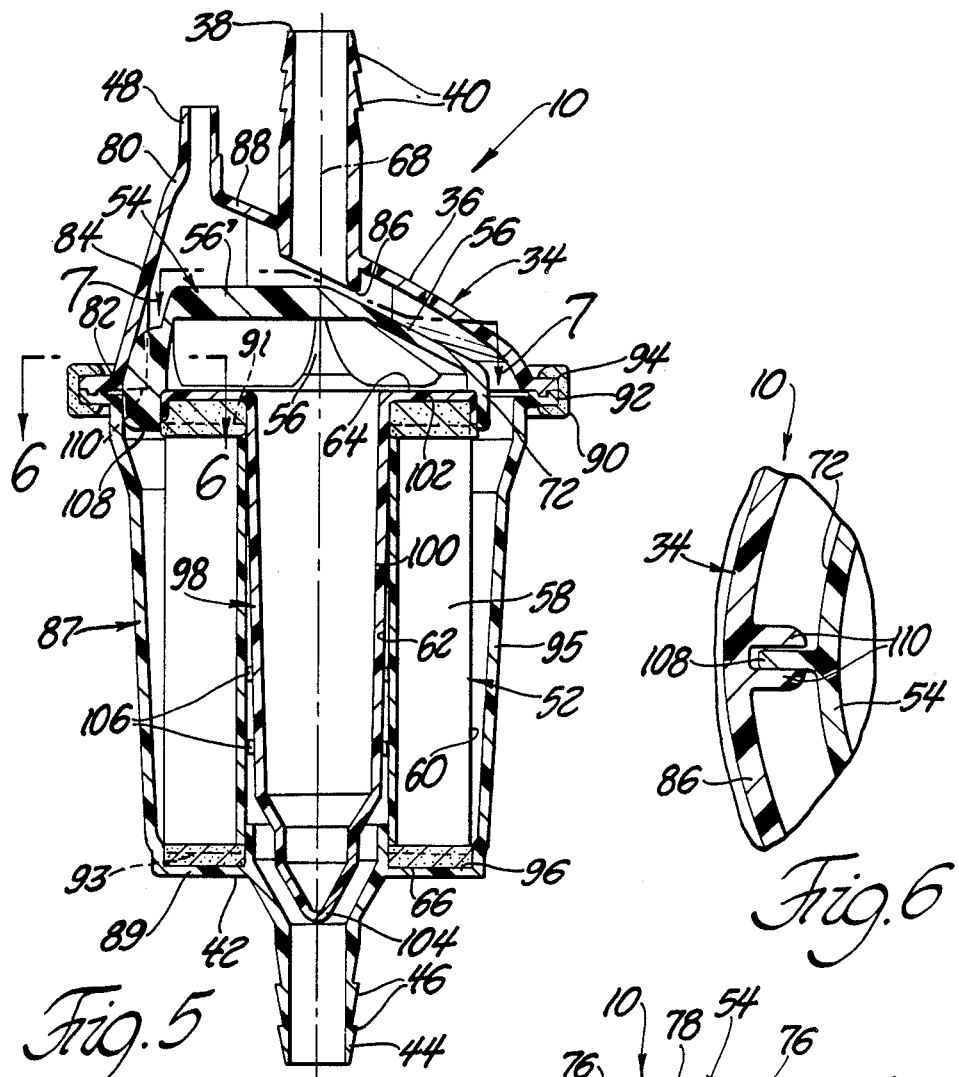
Fig. 5
Fig. 6
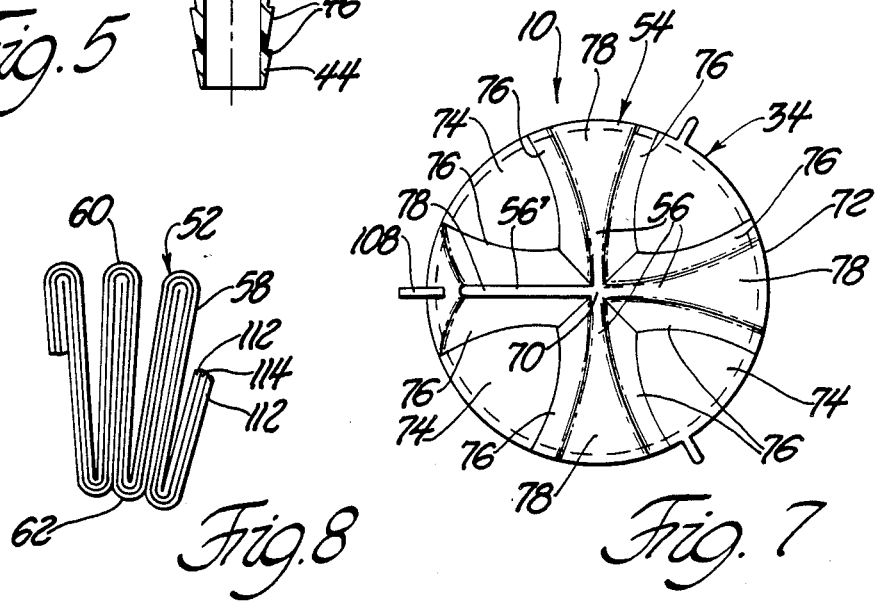
Fig. 8
Fig. 7

ARTERIAL BLOOD FILTER

TECHNICAL FIELD

The subject application relates to a fluid filter. More particularly, the subject application relates to arterial blood filters used in conjunction with heart/lung machines during open heart surgery for the purpose of removing air emboli and other foreign matter prior to re-entry of the blood into the patient's vascular system.

BACKGROUND ART

Arterial blood filters can be used in conjunction with a heart/lung machine during open heart surgery, along with a number of other devices. The purpose of this equipment is to take over the function of the heart and lungs during open heart surgery so that the heart can be repaired with very little interference by the peritoneal blood, thereby providing a clear field for the surgeon. The arterial filter is the last device through which the blood passes before being returned to the patient. The function of the arterial filter is to remove air emboli and other foreign matter that may be present in the blood, so that these foreign substances do not enter the patient's vascular system.

There have been a number of arterial blood filters on the market over the past years. These filters are generally similar in materials and construction, although the geometry of the designs vary considerably.n In general, these prior art devices utilize polycarbonate resin for the housing because of the need for high impact resistance to adequately resist the impacts and abuse which may be experienced during the elimination of trapped bubbles in the priming process by tapping on the devices to dislodge the bubbles. The filter media is generally monofilament polyester screen in the 20-43 micron pore size range and is sandwiched with an inner and outer layer of polypropylene netting before being pleated and formed into a cylindrical pack. The function of the netting is to lend mechanical stiffness to the pleated pack. The pleated filter media packs are set into the housing with a potting compound, which is generally an olefin hot melt or polyurethane. The housing parts are joined together by a variety of methods, including spin welding, ultrasonic welding, hot plate welding, electromagnetic fusion, and screw type assemblies.

The assemblies generally include a blood inlet and a blood outlet. The blood inlets are in various positions and attitudes. Some of the inlets take the form of a connector which is tangent to the outer cylindrical wall of the housing, thus causing a vortex type flow for the purpose of forcing bubbles to the center and top of the filter housing where they can exit the filter through a vent fitting. The U.S. Pat. No. 4,411,783 to Dickens et al, issued Oct. 25, 1983, is an example of such an assembly. Other designs of arterial blood filters make use of an axial inlet which is at the top of the filter, the blood entering and flowing in an end to end path to an outlet connector at the bottom. The U.S. Pat. No. 4,056,476 to Mouwen et al, issued Nov. 1, 1977 is an example of an arterial blood filter having axial inlets and outlets and a vent disposed at the inlet end of the assembly.

Several problems are encountered in prior art arterial blood filter assemblies which demand improvement. Of primary importance is the venting of air emboli from the filter housing. The air emboli must be efficiently removed from the housing, and foreign matter trapped by the media, while hemolysis must be avoided. Additionally, it is necessary that the external blood circuit outside of the patient's body must consume as little blood volume as possible in order to not deprive the patient of the patient's own blood volume and require additional blood, saline or other volume enhancers to be fed into the patient's cardiovascular system. Hence, it is critical that the arterial blood filter have the minimum possible blood volume.

The present invention provides a novel and efficient means for enhancing the removal of air emboli from the filter assembly. Additionally, the specific construction of the assembly results in a minimum internal volume of the blood filter assembly.

STATEMENT OF THE INVENTION

According to the present invention, there is provided an arterial blood filter assembly for removing undissolved gases from blood flowing through the assembly. The assembly includes a housing. The housing includes a first end having a blood flow inlet and a second end having a blood flow outlet and vent means in the first end of the housing and spaced from the inlet for venting undissolved gases from the housing. Filter means is supported within the housing for filtering undissolved gases from the blood flow. The filter means includes an inlet side surface for initially receiving the blood flow from the inlet and an outlet side surface releasing the blood flow to the outlet. The assembly is characterized by including blood dividing means disposed between the inlet and the filter means for dividing the blood flow from the inlet into a plurality of spaced inlet streams flowing over and partially through the inlet side surface of the filter means to the outlet, and for forming the remaining portion of the blood flow containing the undissolved gases into return streams over the inlet side surface between the spaced inlet streams to the vent means where the undissolved gases are vented from the housing.

The present invention further provides a method for removing undissolved gases from flowing blood in a filter assembly, the method including the steps of dividing the inlet blood flow into the assembly into a plurality of spaced inlet streams and filtering the undissolved gases from the flowing blood. A portion of the blood flow containing the filtered undissolved gases is formed into return streams between the spaced inlet streams. The undissolved gases from the return streams are collected, condensed, and are then vented from the filter assembly.

FIGURES IN THE DRAWINGS

Other advantages of the present invention will be readily appreciated as the same becomes better understood by reference to the following detailed description when considered in connection with the accompanying drawings wherein: FIG. 1 is a schematic diagram of a patient connected to a heart/lung machine system;

FIG. 2 is an elevational view partially broken away of the subject invention viewed substantially along lines 2—2 of FIG. 1;

FIG. 3 is a cross sectional view taken substantially along lines 3—3 of FIG. 2;

FIG. 4 is a top plan view taken substantially along lines 4—4 of FIG. 2;

FIG. 5 is a cross sectional view taken substantially along lines 5—5 of FIG. 2;

FIG. 6 is an enlarged fragmentary cross sectional view taken substantially along lines 6—6 of FIG. 5;

FIG. 7 is a cross sectional view taken substantially along lines 7—7 of FIG. 5; and FIG. 8 is an enlarged fragmentary cross sectional view of the filter media.

DETAILED DESCRIPTION OF THE DRAWINGS

Figure 1:
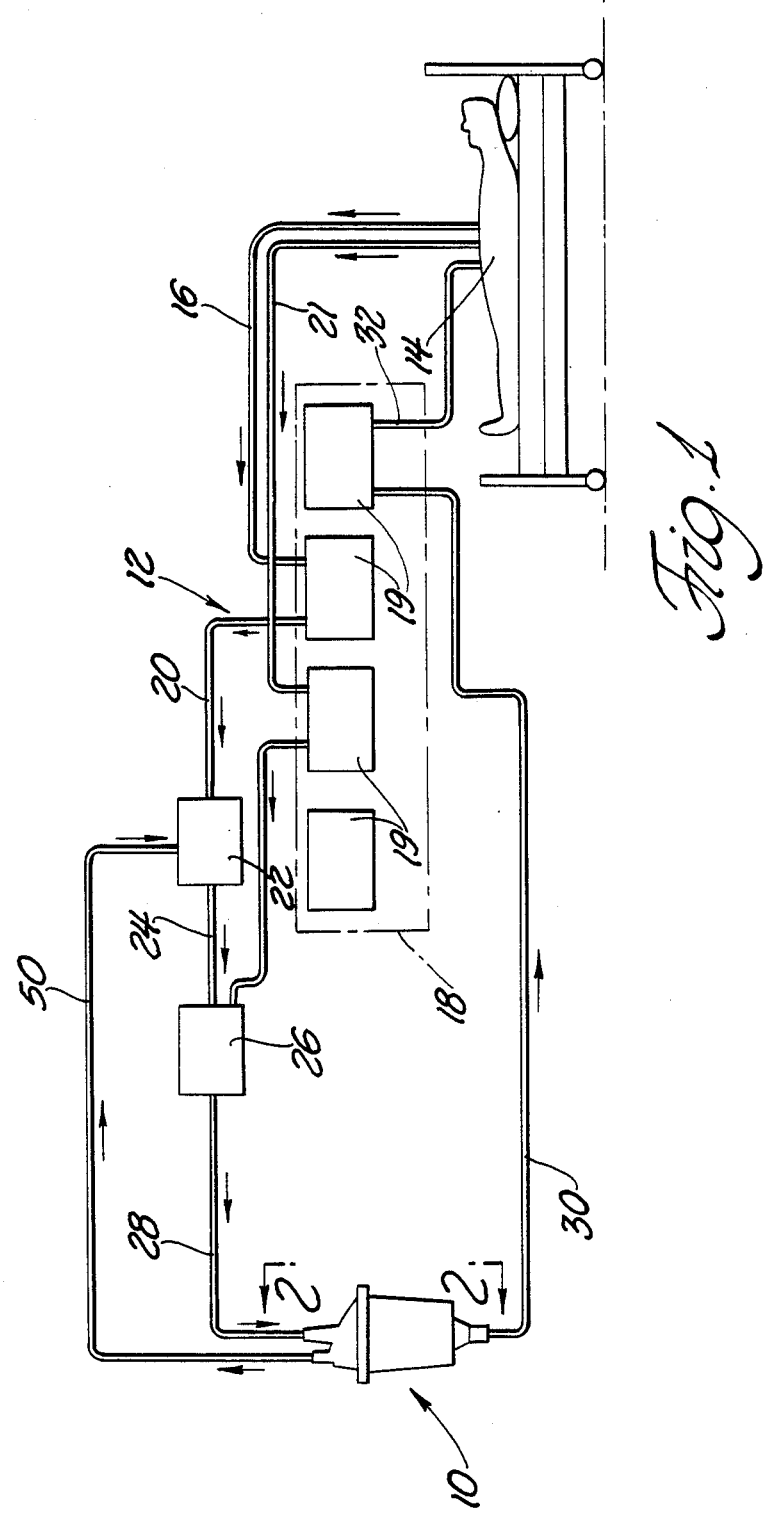

An arterial blood filter assembly constructed in accordance with the present invention is generally shown at 10 in the Figures.

FIG. 1 schematically depicts the arterial blood filter assembly 10 connected in series with a heart/lung machine setup generally shown at 12. A patient 14 has an open thoracic cavity during surgery. A suction line 16 for removing blood from the thoracic cavity is connected to the heart/lung machine 18. The heart/lung machine can comprise four or five pumps 19 in a common console and have a plurality of devices mounted thereon. A fluid line 20 runs from the heart/lung machine 18 to a cardiotomy reservoir 22. The reservoir 22 includes filter mechanisms for filtering the blood of the various foreign matter. The filtered blood is then carried in line 24 to an oxygenator 26 which reoxygenates the filtered blood. Also being fed to the oxygenator by another pump of the heart lung machine is blood from the patient's vena cava through line 21. In this oxygenation process, the blood is cooled and oxygen is mixed with the blood, commonly by a bubbling process. The blood is then carried through fluid line 28 to the arterial blood filter 10. The arterial blood filter 10 removes any oxygen not dissolved in the oxygenated blood and further removes other foreign particulate matter. Line 30 then carries the filtered blood back through the heart/lung machine 18 and the blood is returned to the patient's aorta by line 32. Small amounts of blood containing the undissolved oxygen are vented from the arterial filter 10 and returned through fluid line 50 to the oxygenator 22 for recycling. Of course, FIG. 1 shows schematically a general setup. The assembly 12 can include more bypasses and pumping mechanisms as well as other filtering devices. However, FIG. 1 depicts a general heart/lung machine setup wherein blood is filtered, oxygenated and then the oxygenated blood is filtered again to remove undissolved oxygen from the blood.

The arterial blood filter assembly 10 removes undissolved gases from the blood flowing through the assembly 10. Generally, the assembly 10 includes a housing generally indicated at 34. The housing 34 includes a first end 36 having a blood flow inlet 38. Blood initially enters the housing 34 through the inlet 38. The blood flow inlet 38 can include a plurality of annular ridges 40 extending therefrom and adapted for retaining tubing over the inlet 38. The housing 34 includes a second end 42 having a blood flow outlet 44. Filtered blood leaves the assembly 10 through the outlet 44. The blood flow outlet also can include annular ridges 46 extending radially therefrom for retaining a tube member thereon.

The blood flow inlet 38 receives blood from the tubing 28 and is connected thereto while the blood flow outlet 44 allows for the removal of blood from the housing 34 and into the fluid tubing 30. The housing 34 includes a vent port 48 in the first end 36 of the housing 34, the vent port 48 being spaced from the inlet 38 for venting undissolved gases from the housing 34. As shown in FIG. 1, the vent port 48 is connected to tubing 50 for returning the blood containing the undissolved gases, most typically oxygen, from the housing 34 to the cardiotomy reservoir 22. The cardiotomy reservoir 22 then refilters the blood and further returns the blood to the oxygenator 26 for remixing of the blood with oxygen.

The assembly 10 includes filter means generally indicated at 52 supported within the housing 34 for filtering the undissolved gases and other foreign matter from the blood flow. The filter means 52 is a filter pack supported within the housing 34 and generally includes an inlet side surface 60 for initially receiving the blood flow from the inlet 38 and an outlet side surface 62 for releasing the blood flow to the outlet 44.

The assembly 10 includes blood flow dividing means generally indicated at 54 disposed between the inlet 38 and the filter means 52 for dividing the blood flow from the inlet 38 into a plurality of spaced inlet streams (shown by the downward arrows in FIG. 2) flowing over and through the inlet side surface 60 of the filter means 52 to the outlet 44, and for forming the remaining portion of the blood flow containing the undissolved gases into return streams (indicated by the upward arrows in FIG. 2) over the inlet side surface 60 between the spaced inlet streams. These return streams join and the undissolved gases are collected and condensed prior to being vented from the housing 34 at the vent port 48 through the fluid tubing 50, and to the cardiotomy reservoir 22. In other words, the blood flow dividing means separates and spaces the downward or inlet flow of blood over the filter into separate streams. Although there may be some downward flow between these streams, it is of a lower relative velocity whereby blood containing air bubbles can rise over these lower velocity streams and be vented through the vent port 48. The undissolved gases are vented in the form of bubbles densely entrained in a small portion of the blood.

More particularly, the blood flow dividing means 54 includes a plurality of vanes 56 disposed between the inlet 38 and the filter means 52. The filter means 52 includes a substantially cylindrical shaped pleated filter media 58 having an outer surface 60 including the aforementioned inlet side surface of the filter means 52 and an inner surface 62 including the aforementioned outlet side surface. The filter means 52 has a first end 64 adjacent the inlet 38 and a second end 66 adjacent the outlet 44. The blood flow dividing means 54 is shown in FIG. 5 to be cap member 54 mounted on the first end 64 of the filter means 52.

The housing 34 has a central longitudinal axis shown in phantom as 68 in FIG. 5. The inlet 38 and outlet 44 are on the central axis 68. The blood flow dividing means 54 is substantially circular, as shown in FIG. 7 in plan view, and has a center point 70 on the central axis 68. The vanes 56 include a single origin at the center point 70 on the central axis 68 and eminate radially from the origin or center point 70. As best seen in FIG. 7, the assembly 10 includes four vanes 56 spaced equally from each other extending from the center point 70.

The blood flow dividing means 54 includes an annular perimeter 72, as shown in FIGS. 5 and 7, the perimeter 72 being adjacent to the outer surface 60 of the filter media 58. The vanes 56 extend radially from the center point 70 to the annular perimeter 72.

The vanes 56 form channels or valleys 74 therebetween. Each of the vanes 56 have sloped side surfaces 76, as shown in FIG. 7. Each of the vanes 56 have a top surface 78 extending between each of the side surfaces 76. Blood flows from the inlet 38 over the origin 70 and is divided by the vanes 56 into separate and spaced inlet blood flow streams over the recesses 74 and onto the outer surface 60 of the filter media 58 through which undissolved gases do not readily pass.

In operation, the blood flow carries the undissolved gases in return streams between the inlet streams back over the outer surface 60 of the filter media 58 and over the top surfaces 78 of the vanes 56 and out through the vent port 48.

The top surfaces 78 of each of the four vanes 56 are sections of a conical surface.

The first end 36 of the housing 34 is a dome including a peak at 80, as shown in FIG. 5. The housing 34 further includes a substantially annular peripheral edge 82 and a sloped surface 84 extending therebetween. The peak 80 is offset from the central axis 68. The vent port 48 extends from the peaked portion 80 of the dome and the inlet 38 is disposed on one of the sloped surfaces 84. An annular flange 86 extends into the dome from the inlet 38 whereby blood flowing along the somewhat curved upper sloped surface 84 does not obstruct the inlet flow of blood through the inlet 38 but rather flows around the inlet to the vent port 48.

Three of the vanes 56 have a substantially similar predetermined height measured from the recesses 74 towards the first end 36 of the housing 34. The top surfaces 78 of each of the vanes 56 is spaced from the sloped sides 84 of the domed first end 36. One of the vanes 56' has a respectively greater height and extends into the peaked portion 80 of the dome and is spaced therefrom. In this manner, each of the vanes 56,56' is in close proximity with the domed first end 36 of the housing 34 thereby minimizing the internal volume of the filter assembly 10. By minimizing the internal volume of the filter assembly 10, the internal volume of the entire heart/lung machine system 12 is not significantly increased thereby keeping the volume of blood outside the patient to a minimum.

The housing 34 includes a body member generally indicated at 87 and a cover 88. The body member 87 includes a closed end 89 having the outlet 44 extending therefrom and an open end. The open end includes connecting means for connecting the body member 87 to the cover 88. The connecting means includes an annular seal 90 molded over the peripheral ends 92 and 94 of the body 87 and cover 88 respectively. Other means may be utilized to connect the cover 88 to the body 87. Preferably, the connecting means should perfect a seal effectively creating a unitized housing assembly 34.

The body 87 has inwardly tapering side walls 95. The space between the outer surface 60 of the filter media and the side walls 60 tapers downwardly.

The cover 88 includes the inlet 38 and vent port 48. The cover 88 defines the aforementioned dome.

The assembly 10 includes filter media support means for supporting the filter media 58 within the body member 87 of the housing 34. The filter media 58 includes first and second ends 91,93, as shown in FIG. 5. The filter media 58 further includes a hollow tubular center portion defined by the inside surface 62 thereof. The filter media support means includes an annular trough portion 96 extending into the body member 87 from the closed end portion 89 of the body member 87. The second end 93 of the filter media 58 is fixedly secured within the trough portion 96, usually by a potting compound or other adhesive common in the art. The filter media support means further includes a support member generally indicated at 98 having a tapered tubular midportion 100 extending through the center portion of the filter media 58 and a flanged end portion 102 fixedly containing the first end 91 of the filter media 58. A substantially conically shaped end portion 104 extends from the midportion 100 towards and is spaced from the outlet 44. This construction of the filter media support means further contributes to the limited internal volume of the assembly 10 by creating a closed internal void.

The assembly 10 optionally includes spacing means for spacing the inner surface 62 of the filter media from the midportion of the support member 98. The spacing means includes a plurality of ribs 106 extending radially outwardly from the midportion 100. The blood flows through the filter media 58 and around the ribs 106 to the outlet 44.

The blood flow dividing means 54 is a cap member 54 mounted on the flanged portion 102 of the filter media support member 98.

The assembly 10 includes alignment means for aligning the cover 88 with the cap member 54. The alignment means, shown in FIG. 6, includes a radially outwardly projecting rib 108 adjacent to the periphery 72 of the cap member 54. The cover 88 includes a pair of spaced ribs 110 defining a seat therebetween. The rib 108 of the cap member 54 is seated within the seat defined by the ribs 110 thereby preventing rotation of the cap member 54 and aligning the cap member 54 with the cover 88 during assembly.

The filter media 58 includes two outer layers 112 of polypropylene screen and a monofilament polyester screen 114 sandwiched therebetween, as shown in FIG. 8.

In operation, blood passes over the cap 54 which covers the flanged portion 102 of the filter media support means 98. The blood flows down the outside of the pleated media 52, through the media and out the centrally disposed outlet 44 at the bottom of the housing 34. The cap member 54, which the blood contacts immediately upon entering the filter assembly 10, includes the four vanes 56 which tend to separate the blood into four streams, which are radially separated 90° from each other. These streams flow down the outside 60 of the pleated media 52 into the tapering space between the filter media 52 and the side wall 95 of the body 87 causing the streams to spread sideways and meet, thereby forming upward flowing streams which carry the entrained bubbles upward. Between these streams, blood flow tends to be at a lower velocity and in an upward direction, so that bubbles can rise to the top and collect there and pass out through the vent 48. The media itself is a 21 micron pore size monofilament polyester screen 114 sandwiched between the two layers of polypropylene netting 112. Media of other suitable pore size may be used such as 33 or 43 micron pore sizes.

In order to keep constant velocity of the blood and prevent flow stagnation, the space between the filter media 58 and the housing 34 decreases towards the second end 42 of the housing 34. Additionally, the priming volume, also called the void volume, is kept as small as possible so that as much of the patient's blood as possible is kept within the patient's body. The assembly 10 includes a straight sided media pack 58 and tapered housing body 86 which contributes to the lower void volume. The present invention provides efficient removal of gases from the filtered blood while further providing a minimum size void volume.

The present invention further provides a method for removing undissolved gases from flowing blood in the filter assembly 10. The method includes the steps of dividing the inlet blood flow into the assembly 10 into a plurality of spaced inlet streams and filtering the undissolved gases from the flowing blood. A portion of the blood flow containing the undissolved gases is formed into the return streams between the spaced inlet streams, as best illustrated in FIG. 2. The return streams are vented from the assembly 10 through the vent port 48. More specifically, the dividing step is further defined as dividing the blood flow from the inlet 38 into the plurality of inlet streams flowing over and through the inlet side surface 60 of the filter media 58 to the outlet 44. The return streams are formed to flow upwardly over the inlet side surface 60 of the filter media 58.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An arterial blood filter assembly (10) for removing undissolved gases from blood flowing through said assembly (10), said assembly (10) comprising: a housing (34) including a first end (36) having a blood flow inlet (38) and a second end (42) having a blood flow outlet (44) and vent means (48) in said first end (36) of said housing (34) and spaced from said inlet (38) for venting undissolved gases from said housing (34); filter means (52) supported within said housing (34) for filtering undissolved gases from the blood flow, said filter means (52) including an inlet side surface (60) for initially receiving the blood flow from said inlet (38) and an outlet side surface (62) for releasing the blood flow to said outlet (44); and characterized by blood flow dividing means (54) disposed between said inlet (38) and said filter means (52) for dividing the blood flow from said inlet (38) into a plurality of spaced inlet streams flowing over and partially through said inlet side surface (60) of said filter means (52) to said outlet (44), and for forming a portion of the blood flow containing the undissolved gases into return streams over said inlet side surface (60) between said spaced inlet streams to said vent means (48) where the undissolved gases are vented from said housing (34).

2. An assembly (10) as set forth in claim 1 further characterized by said blood flow dividing means (54) including a plurality of vanes (56,56') disposed between said inlet (38) and said filter means (52).

3. An assembly (10) as set forth in claim 2 further characterized by said filter means (52) including a substantially cylindrically shaped pleated filter media (58) having an outer surface (60) including said inlet side surface and an inner surface (62) including said outlet side surface, said filter means (52) having a first end (64) adjacent said inlet (38) and a second end (66) adjacent said outlet (44), said blood flow dividing means (54) being mounted on said first end (64) of said filter means (52).

4. An assembly (10) as set forth in claim 3 further characterized by said housing (34) having a central longitudinal axis (68), said inlet (38) and said outlet (44) being on said central axis (68), said blood flow dividing means (54) being substantially circular in plan view and having a center point (70) on said central axis (68), said vanes (56) including a single origin (70) on said central axis (68) and emanating radially from said origin (70).

5. An assembly (10) as set forth in claim 4 further characterized by said blood flow dividing means (54) including an annular perimeter (72) adjacent said outer surface (60) of said filter media (58), said vanes (56) extending radially from said origin (70) to said peripheral perimeter (72).

6. An assembly (10) as set forth in claim 5 further characterized by said blood flow dividing means (54) including a recess (74) between each of said vanes (56,56') defining a bottom of each vane (56,56') and each of said vanes (56, 56') having curving sloped side surfaces (76) and a top surface (78) extending between each side surface (76) whereby blood flows from said inlet (38) over said origin (70) and is divided by said vanes (56,56') into separate and spaced inlet blood flow streams over said recesses (74) and onto said outer surface (60) of said filter media (58) where undissolved gases do not easily pass through, said blood flow carrying the undissolved gases in return streams between the inlet streams back upwardly over said outer surface (60) of said filter media (58) and over said top surfaces (78) of said vanes (56,56') and out said vent means (48).

7. An assembly (10) as set forth in claim 6 further characterized by said top surface (78) of each of said vanes (56,56') being substantially conical.

8. An assembly (10) as set forth in claim 7 further characterized by said first end (36) of said housing (34) being a dome including a peak (80) and a substantially annular peripheral edge (82) and a sloped surface (84) therebetween, said peak (80) being offset from said central axis (68), said vent means (48) being a vent port extending from said peak and said inlet (38) being disposed on said sloped surface (84).

9. An assembly (10) as set forth in claim 8 further characterized by each of said vanes (56) having a substantially similar predetermined height measured from said recesses (74) towards said first end (36) of said housing (34), said surfaces (74,76,78) of said vanes (56) being spaced from said sloped sides (84) of said dome, one of said vanes (56') having a respectively greater height extending into said peaked portion (80) of said dome and being spaced therefrom.

10. An assembly (10) as set forth in claim 9 further characterized by including four of said vanes (56,56') being equally spaced from each other.

11. An assembly (10) as set forth in claim 10 further characterized by said housing (34) including a body member (87) and a cover (88), said body member (87) including a closed end (89) having said outlet (44) and an open end including connecting means for connecting said body member (87) to said cover (88), said cover (88) including said inlet (38) and said vent port (48) and said dome.

12. An assembly (10) as set forth in claim 11 further characterized by said assembly (10) including filter media support means for supporting said filter media (58) within said body member (87) of said housing (34).

13. An assembly (10) as set forth in claim 12 further characterized by said filter media (58) including first and second ends (91,93) and a hollow tubular center portion (95) defined by said inside surface (62) thereof, said filter media support means including an annular trough portion (96) extending into said body member (87) from said closed end portion (89) of said body member (87), said second end (93) of said filter media (58) being fixedly secured within said trough portion (96), said filter media support means further including a support member (98) having a tapered tubular midportion (100) extending through said center portion (95) of said filter media (58) and a flanged end portion (102) fixedly containing said first end (91) of said filter media (58) and a substantially conically shaped end portion (104) of said midportion (100) extending towards and spaced from said outlet (44).

14. An assembly (10) as set forth in claim 13 further characterized by including spacing means for spacing said inner surface (62) of said filter media (58) from said midportion of said support member (98).

15. An assembly (10) as set forth in claim 14 further characterized by said spacing means including a plurality of ribs (106) extending radially outwardly from said midportion (100).

16. An assembly (10) as set forth in claim 15 further characterized by said blood flow dividing means including a cap member (54) mounted on said flanged portion (102) of said filter media support member (98), said cap member (54) including said vanes (56,56') and said recesses (74).

17. An assembly (10) as set forth in claim 16 further characterized by including alignment means for aligning said cover (88) with said cap (54).

18. An assembly (10) as set forth in claim 17 further characterized by said alignment means including a radially outwardly projecting rib (108) adjacent said periphery of said cap member (54) and said cover (88) including a pair of spaced ribs (110) defining a seat therebetween, said rib (108) of said cap member (54) being seated within said seat.

19. An assembly (10) as set forth in claim 18 further characterized by said filter media (58) including two outer layers (112) of a propylene screen and a monofilament polyester screen (114) sandwiched therebetween.

20. An assembly (10) as set forth in claim 1 further characterized by said housing (34) including an inward tapering annular wall (95) defining an inner tapering area between said wall (95) and said inlet side surface (60).

21. A method for removing undissolved gases from flowing blood in a filter assembly (10) said method including the steps of: dividing the inlet blood flow into the assembly (10) into a plurality of spaced inlet streams, filtering the undissolved gases from the flowing blood, forming a portion of the blood flow containing the filtered undissolved gases into return streams between the spaced inlet streams, collecting and condensing the undissolved gases from the return streams, and venting the collected gases from the filter assembly (10).

22. A method as set forth in claim 21 wherein the filter assembly (10) includes an inlet (38) and, outlet (44), a filter media (58) having an inlet side surface (60) and an outlet side surface (62), said dividing step being further defined as dividing the blood flow from the inlet (38) into the plurality of inlet streams flowing over and through the inlet side surface (60) to the outlet (44) and forming the return streams to flow over the inlet side surface (60).

23. A method as set forth in claim 22 wherein the dividing step is further defined as flowing the blood over a plurality of vanes (56,56') disposed between the inlet (38) and the filter media (58).

* * * * *